(12) United States Patent
Ranchod

(10) Patent No.: US 9,220,503 B2
(45) Date of Patent: Dec. 29, 2015

(54) SURGICAL DEVICE FOR CONJUCTIVAL TISSUE CLOSURE

(75) Inventor: Tushar Ranchod, Oakland, CA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 815 days.

(21) Appl. No.: 12/854,433

(22) Filed: Aug. 11, 2010

(65) Prior Publication Data

US 2011/0040307 A1 Feb. 17, 2011

Related U.S. Application Data

(60) Provisional application No. 61/233,621, filed on Aug. 13, 2009.

(51) Int. Cl.
*A61B 17/10* (2006.01)
*A61B 17/08* (2006.01)

(52) U.S. Cl.
CPC .............. *A61B 17/083* (2013.01); *A61B 17/10* (2013.01); *A61B 2017/081* (2013.01)

(58) Field of Classification Search
CPC .. A61B 17/0487; A61B 17/083; A61B 17/10; A61B 17/122; A61B 17/1222; A61B 17/128; A61B 17/1285; A61B 17/0643; A61B 17/0469; A61B 17/064; A61B 17/068; A61B 17/0682; A61B 17/0684; A61B 17/0686; A61B 17/08
USPC ......... 606/139, 142, 151, 154, 157, 158, 213, 606/215–221; 292/256; 29/238, 463; 24/30.5 R, 542, 543
See application file for complete search history.

(56) References Cited

U.S. PATENT DOCUMENTS

| | | | |
|---|---|---|---|
| 2,910,067 A * | 10/1959 | White | 606/221 |
| 3,378,010 A * | 4/1968 | Codling et al. | 606/157 |
| 3,625,220 A | 12/1971 | Engelsher | |
| 4,536,924 A * | 8/1985 | Willoughby | 24/487 |
| 4,612,923 A | 9/1986 | Kronenthal | |
| 4,616,651 A * | 10/1986 | Golden | 606/142 |
| 4,638,804 A * | 1/1987 | Jewusiak | 606/158 |
| 4,646,741 A | 3/1987 | Smith | |
| 4,648,401 A * | 3/1987 | Mattson | 606/174 |
| 4,719,917 A | 1/1988 | Barrows et al. | |
| 4,856,517 A * | 8/1989 | Collins et al. | 606/120 |
| 4,889,119 A | 12/1989 | Jamiolkowski et al. | |
| 4,924,864 A * | 5/1990 | Danzig | 606/142 |
| 4,950,285 A | 8/1990 | Wilk | |
| 5,123,146 A * | 6/1992 | Olson | 24/30.5 R |
| 5,123,913 A | 6/1992 | Wilk et al. | |
| 5,160,339 A * | 11/1992 | Chen et al. | 606/158 |
| 5,282,829 A | 2/1994 | Hermes | |
| 5,366,458 A * | 11/1994 | Korthoff et al. | 606/151 |
| 5,428,871 A * | 7/1995 | Iosif | 24/30.5 R |
| 5,439,479 A | 8/1995 | Shichman et al. | |
| 5,464,416 A * | 11/1995 | Steckel | 606/158 |
| 5,649,937 A * | 7/1997 | Bito et al. | 606/139 |
| 5,960,522 A * | 10/1999 | Boe | 24/543 |
| 6,120,526 A | 9/2000 | Daley | |

(Continued)

*Primary Examiner* — Dianne Dornbusch
(74) *Attorney, Agent, or Firm* — RatnerPrestia

(57) ABSTRACT

Disclosed herein is a surgical device for closing an opening in conjunctival tissue, an instrument for applying the surgical device to close an opening in conjunctival tissue, a system for closing an opening in conjunctival tissue including the surgical device and the instrument, and a method of operating the instrument and the surgical device to close an opening in conjunctival tissue.

11 Claims, 10 Drawing Sheets

(56) References Cited

U.S. PATENT DOCUMENTS

| | | |
|---|---|---|
| 6,692,507 B2 | 2/2004 | Pugsley et al. |
| 6,974,462 B2 * | 12/2005 | Sater .................... 606/232 |
| 7,033,378 B2 * | 4/2006 | Smith et al. ............ 606/220 |
| 7,112,214 B2 | 9/2006 | Peterson et al. |
| 7,992,757 B2 * | 8/2011 | Wheeler et al. ......... 227/176.1 |
| D660,138 S * | 5/2012 | Gallagher et al. ........ D8/383 |
| 2002/0082619 A1 * | 6/2002 | Cabak et al. ............ 606/151 |
| 2004/0059354 A1 * | 3/2004 | Smith et al. ............ 606/151 |
| 2005/0149068 A1 * | 7/2005 | Williams et al. ......... 606/151 |
| 2005/0149069 A1 * | 7/2005 | Bertolero et al. ........ 606/151 |
| 2008/0103510 A1 | 5/2008 | Taylor et al. |
| 2009/0012545 A1 * | 1/2009 | Williamson et al. ..... 606/157 |
| 2009/0209986 A1 * | 8/2009 | Stewart et al. .......... 606/157 |

* cited by examiner

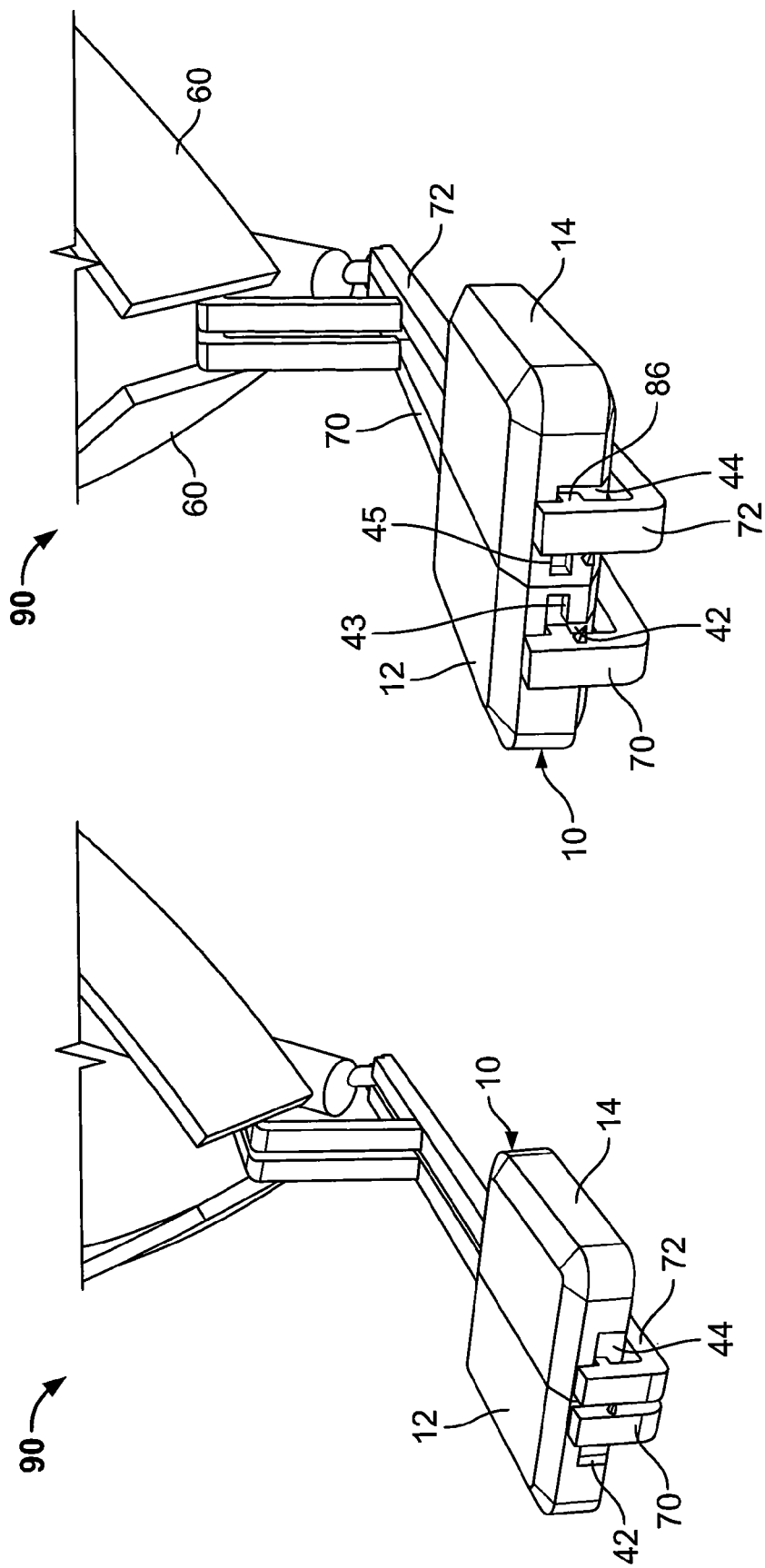

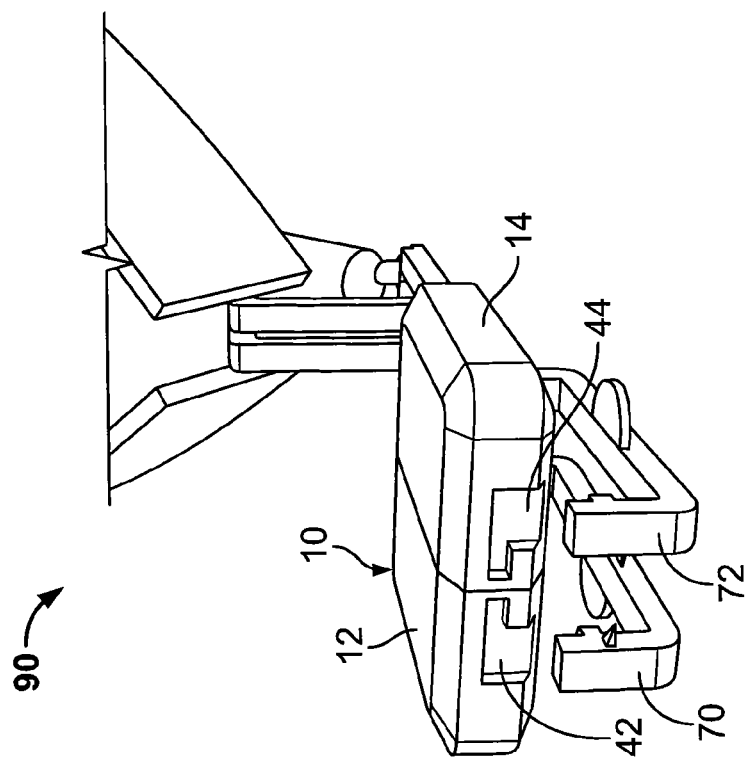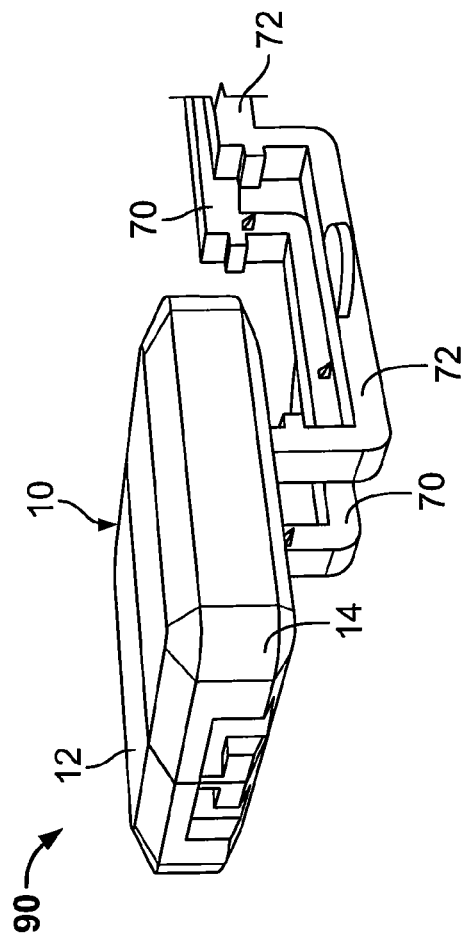

SURGICAL DEVICE FOR CONJUCTIVAL TISSUE CLOSURE

CROSS-REFERENCE TO RELATED APPLICATION

This patent application claims priority to U.S. Patent Application No. 61/233,621, filed Aug. 13, 2009, which is incorporated by reference herein in its entirety.

FIELD OF THE INVENTION

The present invention relates to a surgical device for repairing body tissue such as conjunctival tissue, an instrument for implanting the surgical device, a system for repairing body tissue, and a method for implanting the surgical device.

BACKGROUND OF THE INVENTION

Despite developments made in the past, there remains a continuing need to develop improved tissue closure devices, instruments for implanting tissue closure devices, and methods of implanting the tissue closure devices in the interest of patient safety, patient comfort, ease of installation, installation time, and/or cost, for example. A specific need exists for systems that can be used to close openings in conjunctival tissue.

SUMMARY OF THE INVENTION

According to one aspect of the invention, a device for closing an opening in conjunctival tissue is provided. The device comprises a first component and a second component that are each configured to be positioned beneath conjunctival tissue. The first component includes an absorbable body including a mating surface, a means for connection positioned on the mating surface, and a means for alignment positioned on the mating surface and spaced from the connection means. The second component is configured for mating with the first component. The second component includes an absorbable body including a mating surface. A means for connection is positioned on the mating surface of the second component. The connection means of the second component is configured for connecting the connection means of the second component to the connection means of the first component and for mating the second component to the first component. A means for alignment is positioned on the mating surface of the second component and spaced from the connection means of the second component. The alignment means of the second component is configured for aligning the alignment means of the second component with the alignment means of the first component and for aligning the second component with the first component. Upon alignment between the alignment means of the first component and the second component and connection between the connection means of the first component and the connection means of the second component, the first and second components are secured together and conjunctival tissue can be captivated between the mating surfaces of the first component and the second component.

According to another aspect of the invention, a device for closing an opening in conjunctival tissue is provided. The device comprises a pair of mateable components configured to be positioned beneath conjunctival tissue. Each component has an absorbable body including a mating surface, a connector positioned on the mating surface that is configured for mating with a connector of a mating component, and an alignment element positioned on the mating surface and spaced from the connector for aligning an alignment element of a mating component. The connector of one component is either a recess or a barb configured for engaging the recess and the connector of the other component is the other of the barb or the recess.

According to yet another aspect of the invention, an instrument for applying a surgical device to close an opening in conjunctival tissue is provided. The instrument comprises elongate arms coupled to pivot with respect to each other. Each elongate arm is configured to be positioned beneath conjunctival tissue and has at least one receiving portion for receiving a surgical component. At least one piercing element is positioned on the at least one receiving portion of each arm and extending in a direction toward an opposite elongate arm. The at least one piercing element of each elongate arm is configured for piercing the conjunctival tissue.

According to still another aspect of the invention, a system for closing an opening in conjunctival tissue is provided. The system comprises an instrument comprising a handle for grasping and two elongate arms extending outwardly from the handle and being pivotably coupled with respect to each other about a pivot point. Each elongate arm has at least one receiving portion. At least one piercing element is positioned on the at least one receiving portion of each arm and extends in a direction toward an opposite elongate arm. The at least one piercing element of each elongate arm is configured for piercing the conjunctival tissue upon pivoting the elongate arms in a direction toward each other. A pair of mating components is configured to be positioned beneath conjunctival tissue. Each component is removably positioned on a receiving portion of an elongate arm. Each component has an absorbable body including a mating surface, a connector positioned on the mating surface that is configured for mating with a connector of a mating component, and an alignment element positioned on the mating surface and spaced from the connector for aligning an alignment element of a mating component.

According to yet another aspect of the invention, a method of closing an opening in conjunctival tissue is provided. The method comprises the step of positioning a first component of a surgical device on an elongate arm of an instrument. A second component of the surgical device is positioned on another elongate arm of the instrument. The elongate arms of the instrument are positioned beneath the conjunctival tissue and substantially equidistant from the opening in the conjunctival tissue. A surgical forceps, or other medical instrument, is employed to drape the free edges of the conjunctiva onto piercing elements of each elongate arm. The elongate arms of the instrument are pivoted in a direction toward each other (i.e., closed towards each other) causing the piercing element disposed on each elongate arm to pierce the conjunctival tissue and to draw the conjunctival tissue between a mating surface of the first component and a mating surface of the second component. The elongate arms apply tension to the free edges of the conjunctiva as the elongate arms are brought together, entrapping the free edges of the conjunctiva between the mating surfaces of the components of the device. Pivoting of the elongate arms continues to connect a means for connection of the first component with a means for connection of the second component thereby securing the first component to the second component and captivating the conjunctival tissue between the mating surfaces of the first component and the second component of the surgical device.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures:

FIGS. 8A through 8J depict the steps of an exemplary method of closing a conjunctival opening using a system comprising the instrument of FIG. 3 (a portion of which is illustrated) and the device of FIG. 1, according to aspects of the invention.

More particularly, FIG. 8A depicts the device of FIG. 1 loaded onto the instrument of FIG. 3.

FIG. 8B depicts the device of FIG. 1 positioned beneath conjunctival tissue.

FIG. 8C depicts the elongate arms of the instrument pivoting towards each other and piercing the conjunctival tissue.

FIGS. 8D-8F depict perspective views of the components of the device of FIG. 1 in a mated configuration and the conjunctival tissue captured between the mating surfaces of the components. The conjunctiva is omitted from FIGS. 8E and 8F.

FIG. 8G depicts the elongated arms of the instrument pivoting away from each other. The conjunctiva is omitted from FIG. 8G.

FIG. 8H depicts the elongated arms of the instrument translating in a downward direction thereby entirely disengaging the device of FIG. 1. The conjunctiva is omitted from FIG. 8H.

FIG. 8I depicts the elongated arms of the instrument translating along the lower surface of the device of FIG. 1. The conjunctiva is omitted from FIG. 8I.

FIG. 8J depicts the conjunctival tissue substantially closed by the device of FIG. 1.

DETAILED DESCRIPTION OF THE DRAWINGS

Figure 1:
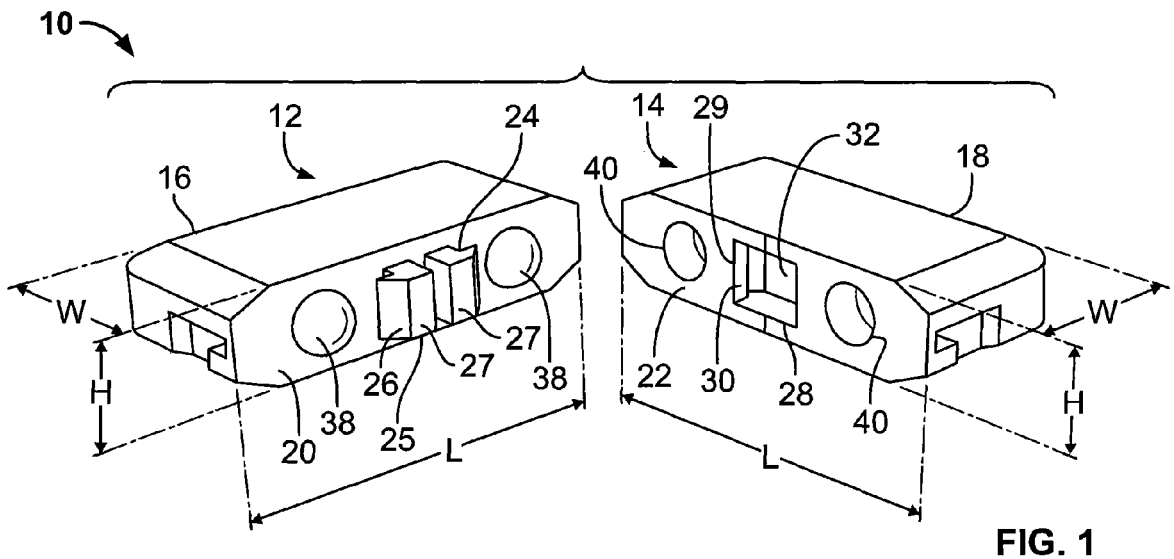
FIG. 1 depicts a perspective view of an exemplary embodiment of a surgical device for closing a conjunctival opening or wound, according to aspects of this invention, wherein the components of the device are shown separated.

Exemplary features of selected embodiments of this invention will now be described with reference to the figures. It will be appreciated that the spirit and scope of the invention is not limited to the embodiments selected for illustration. Also, it should be noted that the drawings are not rendered to any particular scale or proportion. It is contemplated that any of the exemplary configurations and materials and sizes described hereafter can be modified within the scope of this invention.

Surgical fasteners such as staples, clips, clamps, bands, tacks, or other wound or incision closure devices are optionally used in surgical procedures to allow a surgeon to fasten, secure and/or repair body tissue quickly without the need for time consuming suturing.

The goals of tissue closure during ophthalmic surgery differ somewhat from the general goals of skin closure. Several types of ophthalmic surgery entail creating large incisions in the conjunctiva and subsequently closing those incisions. The conjunctiva is a transparent, elastic tissue that covers the bulbar surface of the eyeball as well as the palpebral surface, i.e., the surface on the inside of the eyelid that opposes the eyeball.

Surgeries which require large incisions of the conjunctiva include retina surgeries, such as scleral buckles and 20-gauge vitrectomy; trauma surgery, such as globe exploration or corneoscleral laceration repair; strabismus surgeries; glaucoma surgeries including tube shunts; anterior segment surgeries including excision of conjunctival lesions; and orbital surgeries that utilize a transconjunctival approach. A minority of cataract surgeries using a scleral tunnel or large incision extracapsular extraction also require conjunctival closure.

Because the conjunctiva has sensory innervation and provides a smooth mucous membrane on the external surface of the eye, surgical closure of the conjunctiva preferably utilizes materials that are relatively soft in an effort to avoid painful foreign body sensations for the patient upon movement of the eye. Furthermore, because of the elastic nature of the conjunctiva, the method of closure should be able to withstand some degree of tension without coming apart or tearing the conjunctiva.

To that end, conjunctiva may be closed by absorbable sutures composed of materials such as gut or Vicryl. Suture knots are optionally buried beneath the conjunctiva to minimize surface irritation on the eyeball. But closing a large conjunctival defect may require numerous sutures. While the cost of suture may not be particularly prohibitive, the cost of utilizing an operating room and operating room personnel and consuming anesthesia can be significant for time-consuming surgeries.

Alternatively, thermal cautery is optionally used to close conjunctiva quickly; however, this method may not be sufficient for large closures because the tissue adhesion from cautery may not withstand significant tension. Tissue adhesives such as TISSEEL™, a fibrin glue, may also be used to rapidly close conjunctiva; however, the cost of the TISSEEL™, itself is prohibitive.

FIGS. 1 through 11 illustrate embodiments of tissue closure devices, instruments and systems according to preferred aspects of this invention. Embodiments of a device for closing a superficial elastic layer of living tissue rapidly, under tension if necessary, and without external protrusion of the device, are disclosed in FIGS. 1-2B and 11. The device comprises two components that are designed to mate together using a male-female mechanism, entrapping two free edges of the conjunctival tissue at the mating interface between the components. The device is designed to withstand relatively great tension without failure. The slim profile of the device minimizes any surface irritation and resultant patient discomfort.

An embodiment of an instrument for implanting the device is disclosed in FIGS. 3-7. The instrument has a minimum number of moving parts using a hinge mechanism, and the simple design affords the medical practitioner precise control over implantation of the device.

Embodiments of a system for closing a superficial elastic layer of living tissue rapidly are disclosed in FIGS. 8A-10. The system consists of an instrument for implanting the device, and the device itself which consists of two mateable components. The system for installing the device provides a simple and inexpensive method of conjunctival closure.

A method for closing a superficial elastic layer of living tissue is illustrated in FIGS. 8A-8J. The method comprises the steps of positioning a first component of a surgical device on an elongate arm of an instrument and positioning a second component of the surgical device on another elongate arm of the instrument. The elongate arms of the instrument are positioned beneath conjunctival tissue. Conjunctival tissue is draped over piercing elements of the elongate arms using surgical forceps (or any other medical instrument). The elongate arms are pivoted towards each other, such that the piercing elements hold the free edges of the conjunctiva in place as the conjunctival tissue is drawn between a mating surface of the first component and a mating surface of the second component. The elongate arms of the instrument are pivoted with respect to each other until a means for connection of the first component is engaged with a means for connection of the second component thereby securing the first component to the second component and captivating the wound tissue between the mating surfaces of the first component and the second component. The buried location and slim profile of the device minimize any surface irritation and resultant patient discomfort as well as any risk of device erosion before absorption can occur.

Figure 2A:
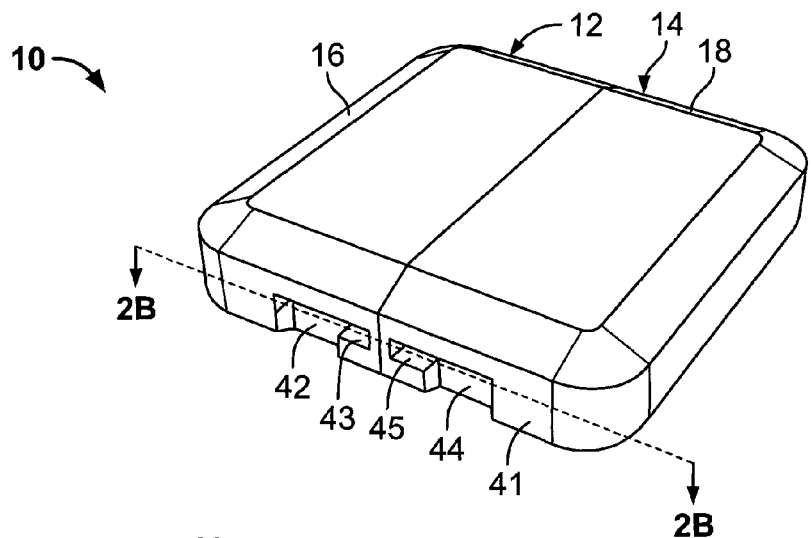
FIG. 2A depicts a perspective view of the surgical device of FIG. 1, wherein the components are depicted in a mated configuration.

FIGS. 1 and 2A depict perspective views of a surgical device for closing a conjunctival opening, according to aspects of this invention. The surgical device is generally represented by the numeral '10.' The device 10 is configured for closing a superficial elastic layer of living tissue rapidly and under tension.

The surgical device 10 includes a pair of mating components 12 and 14. In FIG. 1, the components 12 and 14 of the device 10 are shown separated, whereas in FIG. 2A the components are depicted in a mated configuration. Each component 12 and 14 generally comprises a substantially rectangular-shaped body 16 and 18, respectively. Alternatively, the overall shape of the bodies 16 and 18 may take any other form, such as cylindrical, semi-cylindrical, spherical, semi-spherical, cubic, conical, triangular, or any other desired shape.

The bodies 16 and 18 are preferably low-profile, such that the device 10 does not irritate the eyeball, eyelid or the conjunctiva, thereby minimizing patient discomfort. Moreover, to further minimize any surface irritation, the outer edges of the bodies 16 and 18 are rounded. The bodies 16 and 18 each have a width dimension "W," a height dimension "H," and a length dimension "L." The width "W" of each body 16 and 18 may be about 1 millimeter, for example. The height "H" of each body 16 and 18 may be about 0.5 millimeters, for example. The length "L" of each body 16 and 18 may be about 2 millimeters, for example. It should be understood that the foregoing dimensions are provided for exemplary purposes and may vary depending upon various factors including the size of the opening to be closed, the location of the opening, and other factors.

Each body 16 and 18 includes a mating surface 20 and 22, respectively. As best shown in FIG. 2A, in assembled form of the device 10, the mating surfaces 20 and 22 are positioned to face one another and optionally contact each other. To facilitate mating of the components 12 and 14, each component 12 and 14 includes a connector positioned on the mating surface 20 and 22, respectively, that is configured for mating with a connector of a mating component, as described hereinafter.

The component 12 includes a connector 24 in the form of a barb 25. The barb 25 includes two hooks 27 that extend from the mating surface 20 and are spaced apart along the mating surface 20 by a predetermined distance. The exterior corner of each hook 27 includes a beveled surface 26 for engaging a mating connector of the component 14, as described hereinafter.

The component 14 includes a connector 28 that is configured to mate with the connector 24 of the component 12. The connector 28 of the component 14 is provided in the form of a recess 29. As best shown in the cross-sectional view of FIG. 2B, the recess 29 includes a first opening 30 extending from the mating surface 22 for receiving the beveled surfaces 26 of the barb 25. The width of the first opening 30 is slightly smaller than the distance separating the ends of the beveled surfaces 26. Upon contacting the first opening 30, the hooks 27 of the barb 25 flex in a direction toward each other to fit through the first opening 30.

The first opening 30 of the recess 29 extends into a larger, second opening 32. The width of the second opening 32 is large enough to accommodate the hooks 25 of the connector 26. Once the beveled surfaces 26 clear the opening 30, the hooks 27 deflect back to their original position (as shown in FIG. 1) and are captivated within the recess 29 of the component 14. The component 12 is then mated to the component 14, thereby forming the device 10 shown in FIG. 2A.

The connectors 24 and 28 of the components 12 and 14, respectively, may also be generally referred to herein as a means for connection. The means for connection may be provided in the form of a clip, a pin, a catch, a clamp, a latch, a key, a detent, a fastener, a barb, a hole, an adhesive, a magnet, a slot, a recess, a track, a dovetail or any other connecting device known in the art. Additionally, while each component 12 and 14 includes only one connector 24 and 28, respectively, those skilled in the art will recognize that each component 12 and 14 may include multiple connectors. Also, though the connectors 12 and 14 are illustrated as separate structures, the connector or connection means are optimally combined with an alignment element or alignment means discussed below.

Each component 12 and 14 also includes two alignment elements 38 and 40, respectively. The alignment elements 38 and 40 are provided to facilitate alignment of the components 12 and 14 upon mating. Each alignment element 38 and 40 is positioned on the mating surfaces 20 and 22 of the components 12 and 14, respectively. The alignment elements 38 of the component 12 are positioned on either side of the connector 24, and, similarly, the alignment elements 40 of the component 14 are positioned on either side of the connector 28.

Figure 2B:
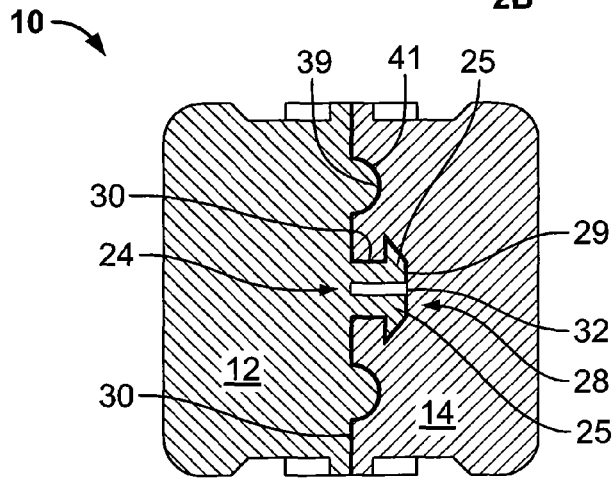
FIG. 2B illustrates a cross-sectional view of the surgical device of FIG. 2A along the lines 2B-2B.
Figure 3:
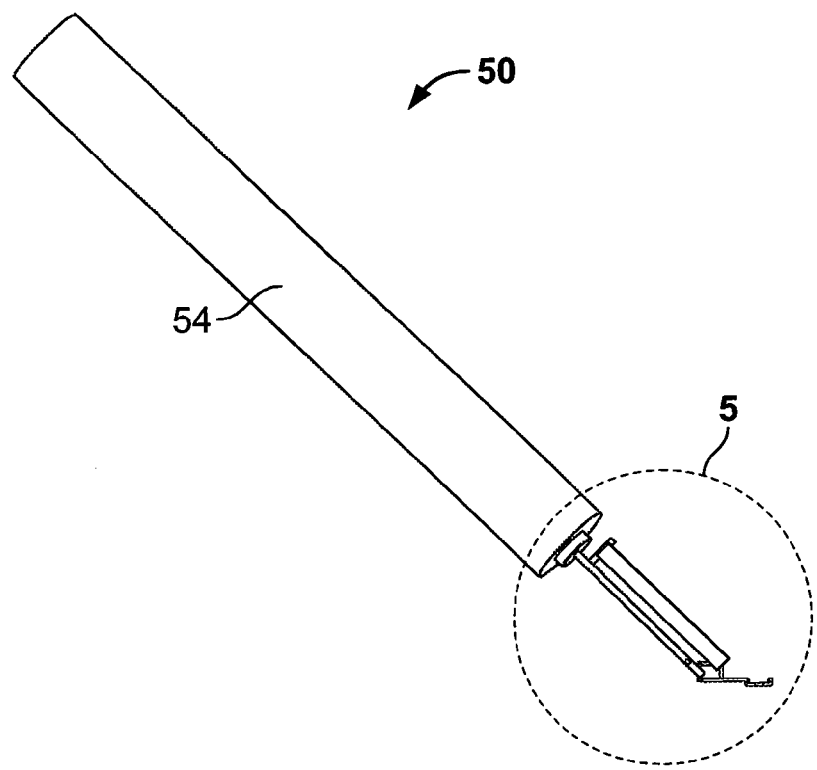
FIG. 3 depicts a left side elevation view of an exemplary embodiment of an instrument for implanting the surgical device of FIG. 1, according to aspects of the invention, wherein the elongated arms of the instrument are illustrated in a closed position.
Figure 4:
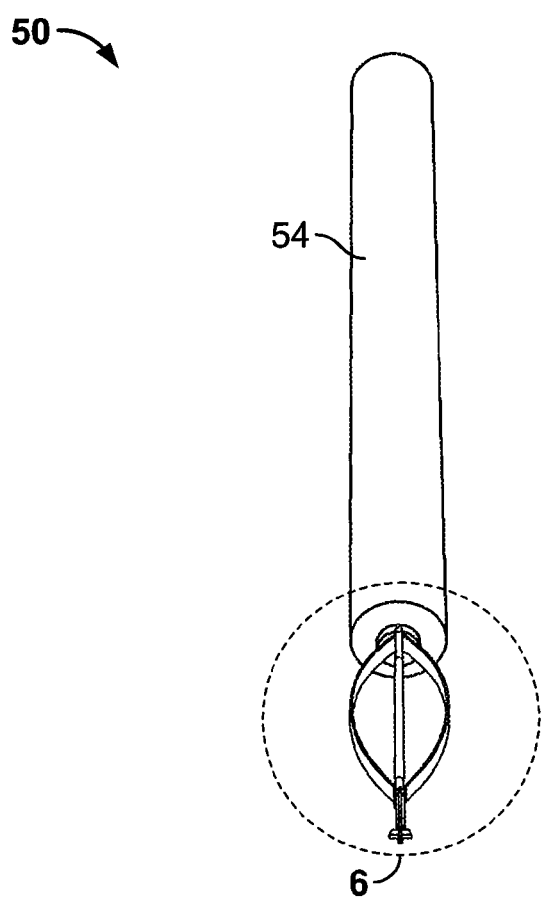
FIG. 4 depicts a front elevation view of the instrument of FIG. 3.

As best shown in FIG. 2B, the alignment elements 38 of the component 12 are provided in the form of semi-spherical detents 39 and the alignment elements 40 of the component 14 are provided in the form of semi-spherical depressions 41 that are sized to accommodate the semi-spherical detents 39.

In assembly, the semi-spherical detents 39 are received in the semi-spherical depressions 41, such that the components 12 and 14 are properly aligned. Moreover, in assembly, the conjunctival tissue is compressed between the alignment elements 38 and 40 such that the conjunctival tissue is firmly captured between the mating surfaces 20 and 22 of the connectors 12 and 14, respectively.

It should be understood that the alignment elements 38 and 40 are not limited to that shown and described herein. The alignment elements 38 and 40 of the components 12 and 14, respectively, may also be generally referred to herein as a means for alignment. The means for alignment may be provided in the form of a post, a hole, a slot, a recess, a pin, a catch, a clamp, a latch, a key, a detent, a fastener, a barb, a hole, a track, a dovetail or any other alignment device known in the art. Additionally, while each component 12 and 14 includes two alignment elements 38 and 40, respectively, those skilled in the art will recognize that each component 12 and 14 may include any number of alignment elements. Alternatively, the alignment elements 38 and 40 may be omitted altogether if so desired.

According to one exemplary use of the device 10, in a mated configuration, conjunctival tissue is captivated between the mating surfaces 20 and 22 of the first component 12 and the second component 14, respectively. Closure of conjunctiva, the superficial elastic tissue layer covering much of the eyeball, is one example in which such a device 10 is useful, but the device 10 is applicable to any surgical procedure involving the closure or repair of a superficial elastic layer of tissue.

Each body 16 and 18 includes an L-shaped recess 42 and 44, respectively, for receiving elongate arms of the instrument shown in FIGS. 3-6. The L-shaped recesses 42 and 44 are formed along the left-side surface 37 and the right-side surface (not shown) of the bodies 16 and 18, respectively. Each L-shaped recess 42 and 44 includes a closed-end 43 and 45, respectively, to temporarily secure the device 10 to the instrument, as described in greater detail with reference to FIG. 8A.

Referring still to FIGS. 1-2B, the bodies 16 and 18 of the components 12 and 14, respectively, are each composed of an absorbable and biologically inert material, such as polyglactin that, which breaks down in the patient's body over a predictable period of time. Material selection for the bodies 16 and 18 is dictated by several parameters. First, the material should be strong and stiff enough to enable coupling of the components 12 and 14 and withstand tension applied by the conjunctival tissue, as described in greater detail with respect to one exemplary use of the device 10. Additionally, as described with reference to FIG. 8D, the connectors 24 and 28 may be formed from a material that is sufficiently strong to pierce the conjunctival tissue upon engagement between both connectors 24 and 28 of the components 12 and 14, respectively. Also, the material should sufficiently flexible to enable limited deflection of the hooks 27 of the connector 24 of the component 12 without fracturing.

The components 12 and 14 of the device 10 may be color-coded such that a medical practitioner can easily distinguish the male component 12 from the female component 14. Alternatively, the components 12 and 14 may be transparent thereby enabling a medical practitioner to view and inspect engagement between the connectors 24 and 28 in an effort to ensure that the connectors 24 and 28 are properly mated.

FIGS. 3-7 depict an instrument for implanting the surgical device 10 of FIGS. 1-2B. The instrument is generally represented by the numeral '50.' The instrument 50 includes a long cylindrical handle 54 for grasping by a medical practitioner. The handle 54 may have ergonomic and aesthetic properties such as a gripping surface formed on or applied thereto to enhance tactile feel. A stem 56 of smaller diameter than the diameter of the handle 54 extends from the cylindrical base 55 of the handle 54.

Figure 5:
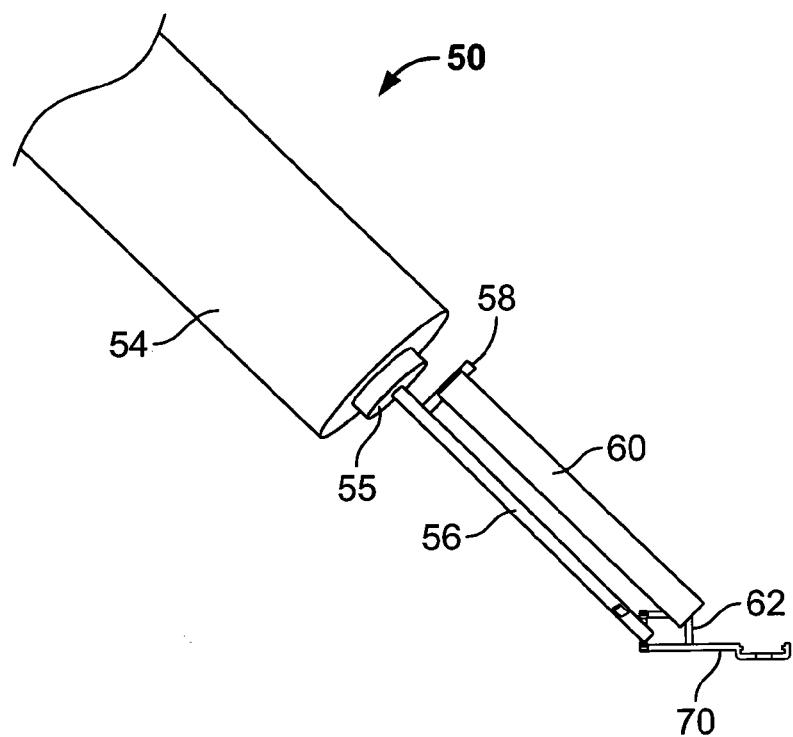
FIG. 5 depicts a detailed view of the instrument of FIG. 3.
Figure 6:
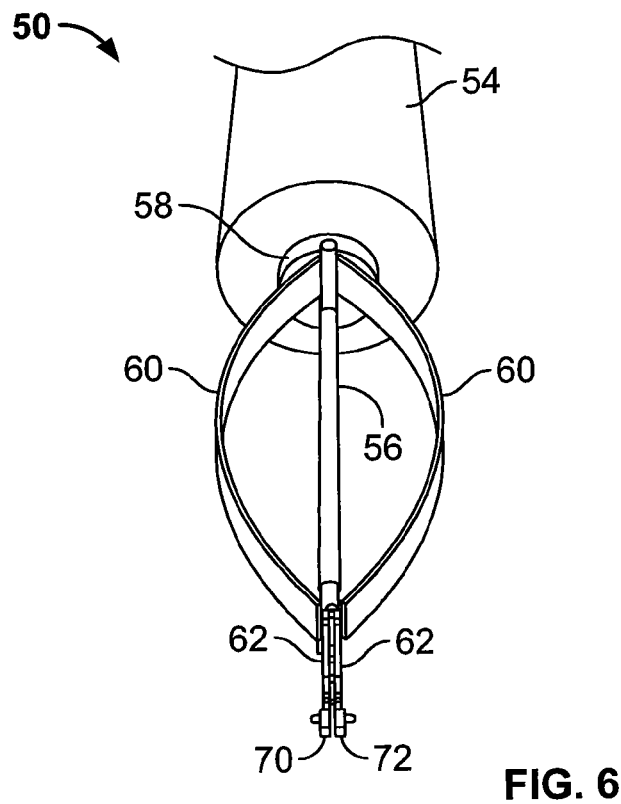
FIG. 6 depicts a detailed view of the instrument of FIG. 4.

A spring support 58 is mounted to and extends from a surface of the stem 56 that is proximal to the handle 54. All references to distal and proximal locations provided herein are defined relative to the handle 54 of the instrument 50. As best shown in FIGS. 5 and 6, two springs 60 are mounted to opposing sides of the spring support 58. The springs 60 may be mounted to the spring support 58, by a weld, for example. Alternatively, the springs 60 may be positioned to bear on the spring support 58. The opposing end of each spring 60 is mounted to an L-shaped support 62.

Figure 7:
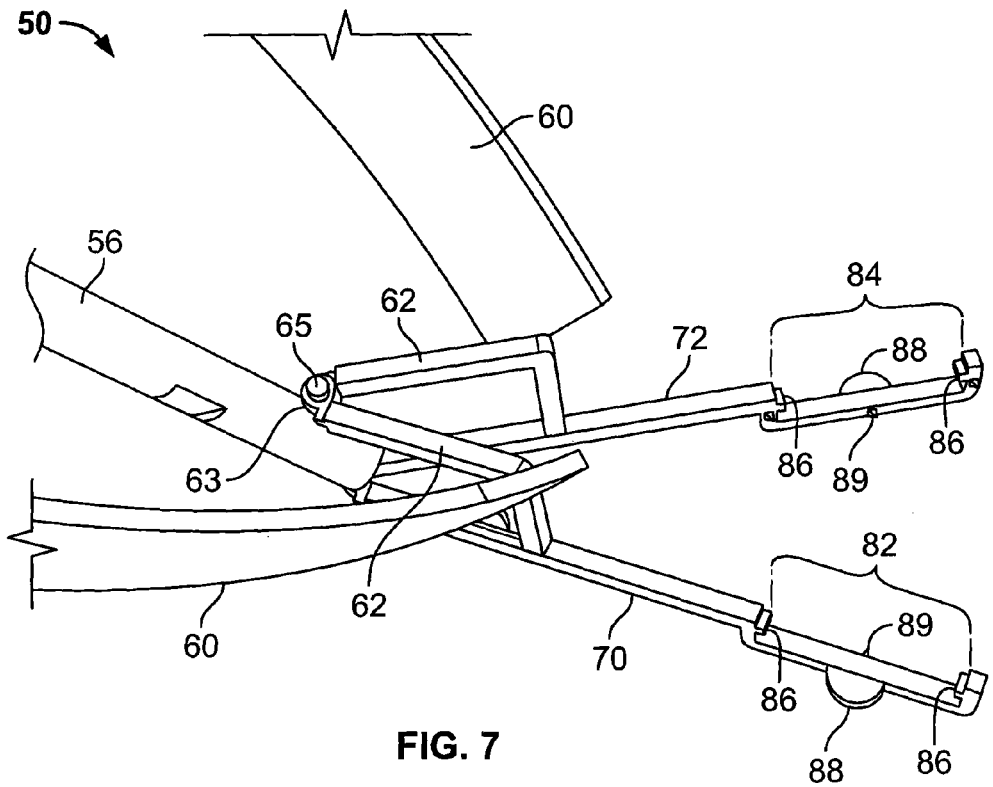
FIG. 7 depicts a partial perspective view of the instrument of FIG. 3 illustrating the elongated arms of the instrument pivoted to an open position.
Figure 8A:
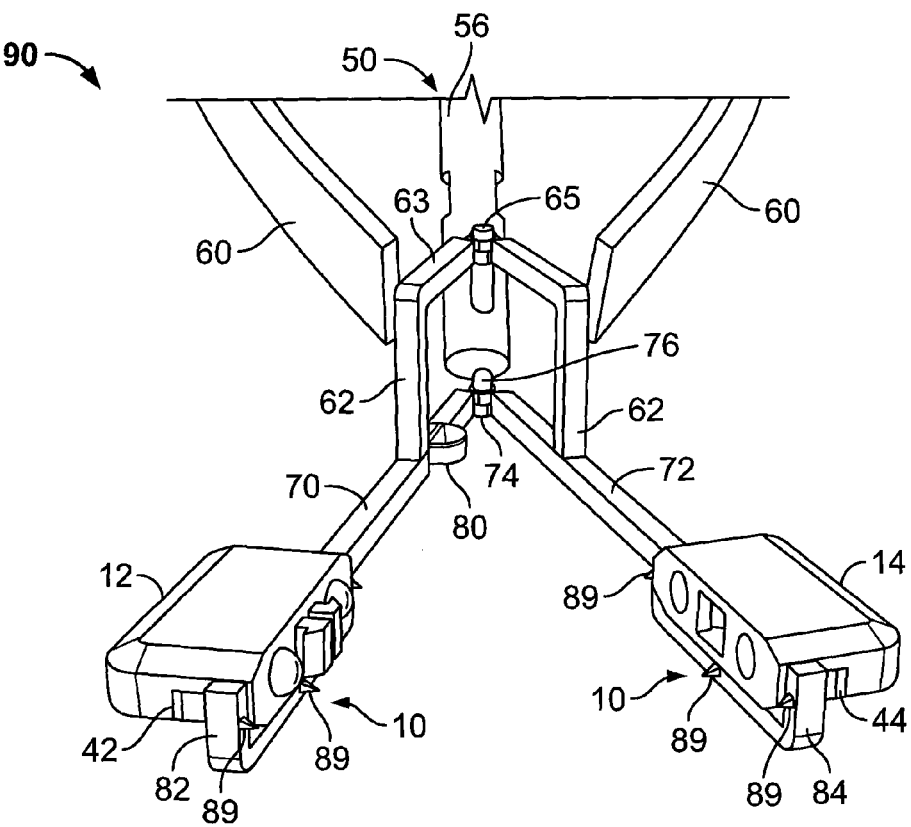

Referring now to FIGS. 5, 7 and 8A, each spring 60 is mounted to a respective L-shaped support 62, by a weld, for example. Alternatively, each springs 60 may be positioned to bear on an L-shaped support 62. The springs 60 are configured to draw the L-shaped supports 62 apart. One end of each L-shaped support 62 is pivotably mounted to the stem 56. That end of each L-shaped support 62 includes a hinge 63 that is positioned to rotate upon a small cylindrical rod 65 that extends from the stem 56. Those skilled in the art will recognize that other ways exist to pivotably mount the L-shaped support 62 to the stem 56. The opposing end of each L-shaped support 62 extends from an elongate arm 70 and 72.

The elongate arms 70 and 72 of the instrument 50 are also pivotably coupled to the distal end of the stem 56, e.g., distal from the handle 54. Each elongate arm 70 and 72 includes a hinge 74 that is positioned to pivot about a rod 76 extending from the distal end of the stem 56, as best shown in FIG. 8A. By using a hinge mechanism, the instrument 50 has a minimum number of moving parts. Those skilled in the art will recognize that other ways exist to pivotably mount the elongate arms 70 and 72 to the handle 54.

As best shown in FIGS. 6 and 7, the springs 60 have a bowed shape to bias the elongate arms 70 and 72 away from each other. The springs 60 may be formed from any resiliently deformable material, such as spring steel. For example, in practice, a medical practitioner manually pushes the springs 60 together to bring the elongate arms 70 together. Accordingly; the exterior surfaces of the springs 60 may have a gripping surface formed on or applied thereto to enhance tactile feel.

As best shown in FIG. 8A, a spring clip 80 is positioned on an interior surface of the elongate arm 70 for biasing the elongate arms 70 and 72 away from each other. The spring clip 80 provides additional resistance in pivoting the elongate arms 70 and 72 towards each other, for smooth pivoting action of the arms 70 and 72. The spring clip 80 may be positioned on either elongate arm 70 or 72. The spring clip 80 may include an adhesive-backed surface for mounting to the interior surface of elongate arm 70. Alternatively, the spring clip 80 may be mounted to elongate arm 70 by a fastener (not shown) or a weld, for example.

Referring now to FIGS. 7 and 8A, a series of piercing elements 89 extend from the interior surface of each elongate arm 70 and 72. Each piercing element 89 extends in a direction toward an opposite elongate arm. The piercing elements 89 are sharp protrusions that are configured for piercing conjunctival tissue, as further described with reference to FIG. 8C. According to the exemplary embodiment of the instrument 50 shown in FIGS. 7 and 8, three piercing elements 89 extend from the interior surface of each elongate arm 70 and 72. The piercing elements 89 are uniformly positioned along the length of a receiving portion 82 and 84 of each elongate arm 70 and 72, respectively. Alternatively, each elongate arm 70 and 72 may include any number of piercing elements 89. The piercing elements 89 may be integral with an elongate arm 70 and 72, or, alternatively, the piercing elements 89 may be fastened to an elongate arm 70 and 72.

As best shown in FIGS. 7 and 8A, each elongate arm 70 and 72 of the instrument 50 includes a receiving portion 82 and 84, respectively, that is configured for releasably receiving and accommodating a component 12 or 14 of the device 10. The component 12 may be arranged in the receiving portion 82 and the component 14 may be arranged in the receiving portion 84, as shown in FIG. 8A, or vice versa.

The receiving portions 82 and 84 each comprises a U-shaped bend formed along a distal portion of an elongate arm 70 and 72, respectively. Two protruding tabs 86 extend from opposite surfaces of each receiving portion 82 and 84. The tabs 86 are provided and sized for engaging a component 12 or 14 of the device 10. Each tab 86 extends across the entire width of each receiving portion 82 and 84 and along a portion of the depth each receiving portion 82 and 84, as shown in FIG. 8I.

A support surface 88 extends outwardly from a central region of each receiving portion 82 and 84. Each support surface 88 has a semi-cylindrical shape. The support surfaces 88 are provided to support and secure the lower surface of a component 12 or 14 of the device 10. The support surfaces 88 may be releasably engaged with either a recess or a hole (not shown) defined on the bottom surface of each component 12 and 14 for added support.

The instrument 50 may be composed of stainless steel to allow sterilization and re-use. The instrument may be alternatively composed of any other material known to those skilled in the art. For example, the instrument could be composed of a polymeric material for disposable use.

The instrument 50 may vary from that shown and described without departing from the spirit or scope of the invention. For example, and although not shown, the instrument 50 could be modified in a manner to facilitate automatic reloading after the delivery of a single device 10, thereby allowing the delivery of multiple devices 10 in rapid succession without manual reloading of the instrument. As another example, the instrument 50 could be modified to load and deliver multiple devices 10 at once, so that a large conjunctival opening could be closed in a single surgical maneuver, as described in greater detail with reference to FIG. 9.

According to one aspect of the invention, as best shown in FIG. 8A, a system 90 is provided for closing a conjunctival opening. The system 90 comprises the instrument 50 and a device 10 including a pair of mating components 12 and 14 provided along with the instrument 50. Each component 12 and 14 is removably positioned on a receiving portion 82 and 84, respectively, of an elongate arm 70 and 72 of the instrument 50. The system 90 is configured to secure one device 10 to conjunctival tissue at one time. Once the device 10 is applied to the tissue layer, a new device 10 is loaded onto the instrument 50.

Figure 9:
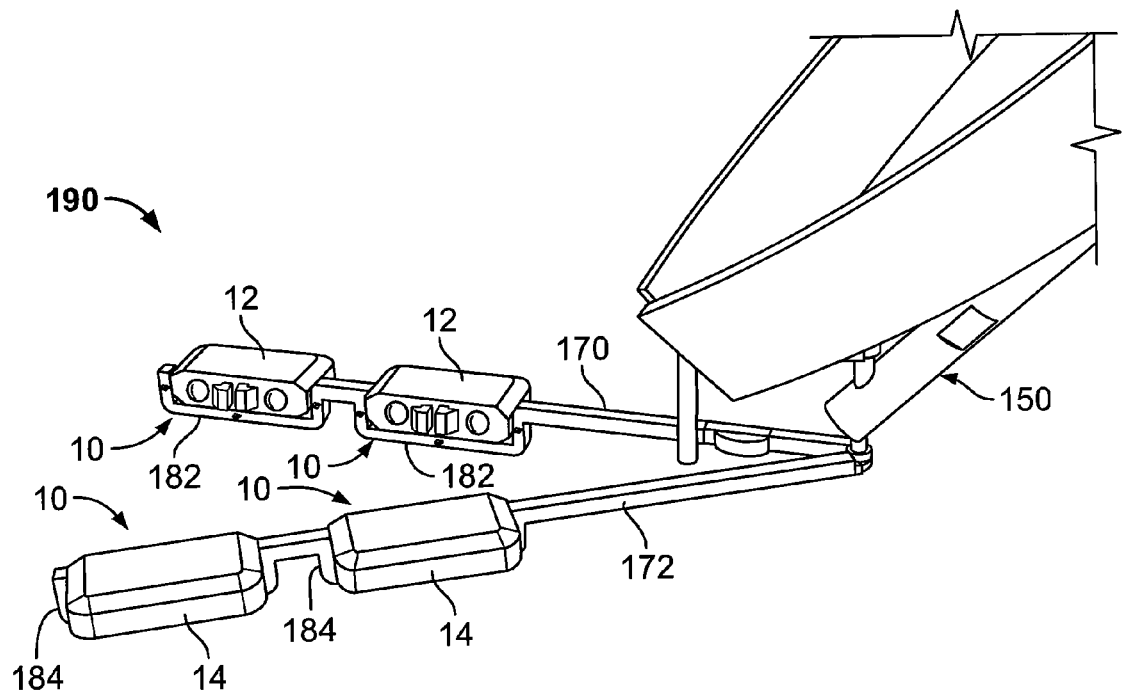
FIG. 9 depicts a perspective view of another system for applying a plurality of surgical devices to close a conjunctival opening, according to another exemplary embodiment of the invention, wherein the exemplary system includes an instrument for applying two of the devices of FIG. 1 and the elongated arms of the instrument are illustrated in an open position.

FIG. 9 depicts another exemplary embodiment of a system 190 for closing a conjunctival opening. The system 190 is substantially similar to the system 90 of FIG. 8A, with the exception that the system 190 is configured to secure two devices 10 to conjunctival tissue in a single surgical maneuver. The instrument 150 varies from the instrument 50 shown in FIGS. 3-7. Each elongate arm 170 and 172 of the instrument 150 includes two receiving portions 182 and 184, respectively, such that two devices 10 may be loaded onto the instrument 150, as shown in FIG. 9.

As described with reference to FIGS. 8A through 8B, the systems 90 and 190 described herein are relatively simple to operate, and confer significant time savings, and thereby cost-savings, as compared with the traditional method of suturing a conjunctival opening. Additionally, the systems 90 and 190 described herein do not require the precise manual dexterity requisite for closing an opening of conjunctiva with sutures.

The systems 90 and 190 may be provided by the manufacturer with the device 10 preloaded onto the instrument 50 and 150, as shown in FIGS. 8A and 9, respectively. Alternatively, the device 10 may be supplied separately from the instrument. Additionally, multiple devices 10 may be pre-packaged together. The individual components 12 and 14 of the device 10 may also be supplied separately.

FIGS. 8A through 8J depict an exemplary method of closing a conjunctival opening using the system 90 comprising the instrument 50 of FIGS. 3-7 and the device 10 of FIGS. 1-2B, according to aspects of the invention. FIGS. 8A through 8F depict an exemplary method of implanting the device 10 and FIGS. 8G through 8I depict an exemplary method of removing the instrument 50 from the device 10 after implantation of the device 10.

FIG. 8A depicts the device 10 of FIGS. 1-2B loaded onto the instrument 50 of FIGS. 3-7. The components 12 and 14 of the device 10 can be loaded onto the instrument 50 manually, for example, by using a small forceps to manually place each component 12 and 14 onto a receiving portion 70 and 72, respectively, of the instrument 50. Alternatively, the device 10 could be pre-seated, as supplied by the distributor, on the instrument 50.

To load the device 10 onto the instrument 10, the open ends of both recesses 42 of the component 12 are slid in a downward direction over the tabs 86 (see FIG. 7) of the receiving portion 82 of the elongate arm 70. The bottom surface (not shown) of the component 12 bears on the support surface 88 of the elongate arm 70. Similarly, the open ends of both recesses 44 of the component 14 are slid in a downward direction over the tabs 86 (see FIG. 7) of the receiving portion 84 of the elongate arm 72. The bottom surface (not shown) of the component 14 bears on the support surface 88 of the elongate arm 72. As stated previously, either the component 12 is loaded onto the elongate arm 70 and the component 14 is loaded onto elongate arm 72 or vice versa, i.e., the component 14 is loaded onto the elongate arm 70 and the component 12 is loaded onto elongate arm 72.

The component 12 is then manually translated forward until the tabs 86 of the elongate arm 70 bear on the closed-end 43 (see FIG. 2A) of both recesses 42, as shown in FIG. 8A. Similarly, the component 14 is also manually translated forward until the tabs 86 of the elongate arm 72 bear on the closed-end 45 (see FIG. 2A) of both recesses 44. The components 12 and 14 of the device 10 are thereafter firmly supported on the receiving portions 82 and 84 of the elongate arms 70 and 72, respectively. The device 10 is then ready for implantation.

Figure 8B:
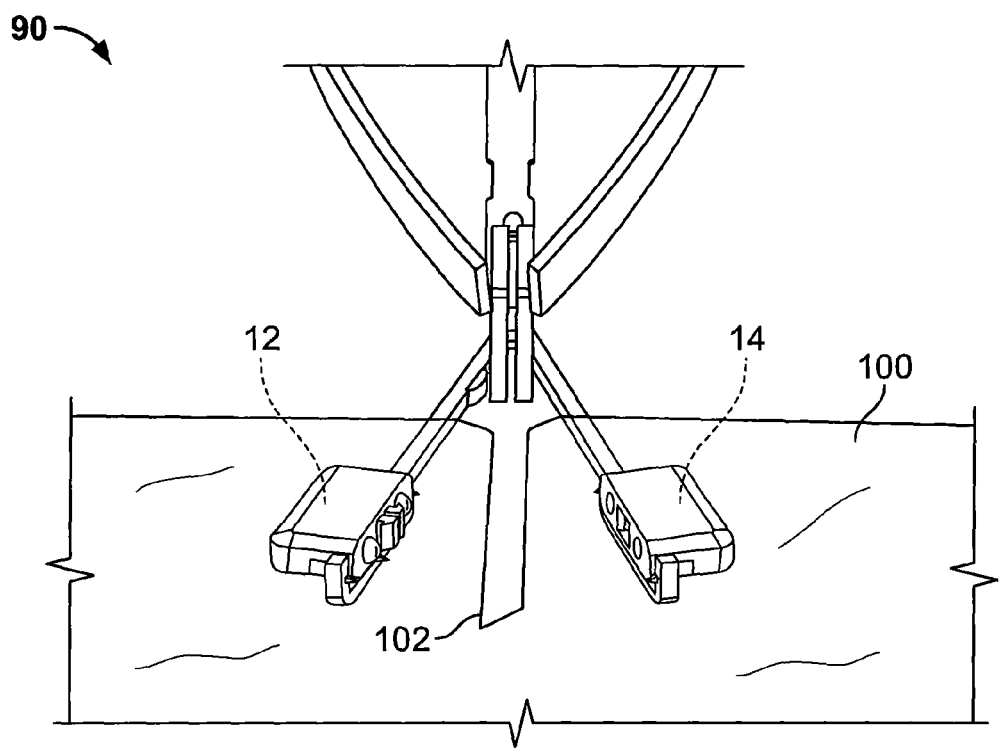

FIG. 8B depicts the device 10 being positioned beneath conjunctival tissue layer 100 (otherwise referred to herein as conjunctiva 100). The device 10 is implanted in such a way that it is buried beneath the conjunctiva 100. In practice, a medical practitioner may raise the conjunctiva 100 with forceps to accommodate the device 10 and the elongate arms 70 and 72 of the instrument 50 beneath the conjunctival tissue layer 100. The components 12 and 14 are then positioned approximately equidistant from the opening 102 of the conjunctiva 100, as shown in FIG. 8B. The opening 102 may otherwise be referred to as a wound.

Figure 8C:
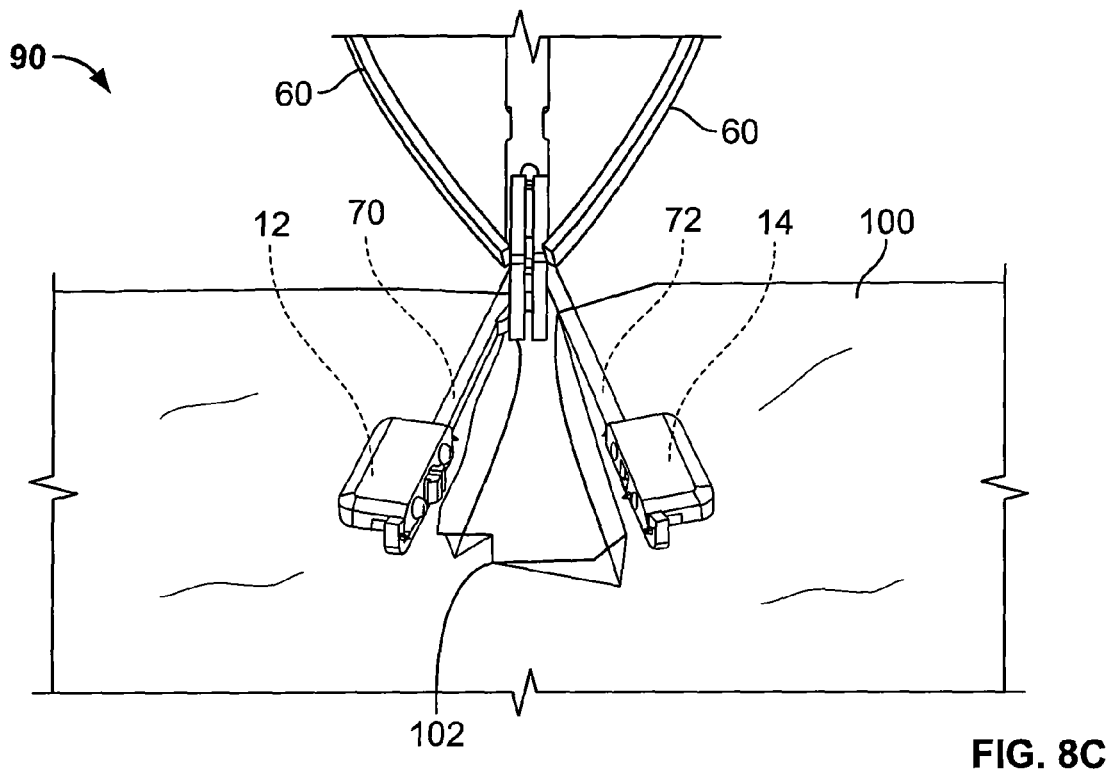

FIG. 8C depicts the elongate arms 70 and 72 of the instrument pivoting towards each other and piercing the conjunctival tissue. In practice, conjunctival tissue is draped over the piercing elements 89 of the elongate arms 70 and 72 using surgical forceps, or any other medical instrument. A medical practitioner manually depresses (i.e., squeezes) the springs 60 of the instrument 50 with his or her fingers consequently pivoting the elongate arms 70 and 72 toward each other. The spring clip 80 (see FIG. 8A) provides additional resistance in pivoting the elongate arms 70 and 72 towards each other, for smooth pivoting action of the arms 70 and 72.

Upon pivoting the elongate arms 70 and 72, the piercing elements 89 (see FIG. 7) of the instrument 50 pierce the conjunctiva 100 consequently drawing the free edges of the conjunctiva 100 in tension between the mating surfaces 20 and 22 (see FIG. 1) of the connectors 12 and 14, respectively. The free edges of the conjunctiva 100 are folded downwards toward the eyeball (not shown) which is located beneath the conjunctiva 100.

Prior to mating the components 12 and 14 together, the alignment elements 38 and 40 (see FIG. 2B) of the components 12 and 14, respectively, engage and facilitate alignment between the components 12 and 14. More particularly, as shown in FIG. 2B, the semi-spherical detents 39 formed in the component 12 engage the semi-spherical depressions 41 of the component 14 thereby compressing the opposing free edges of the conjunctival tissue between the alignment elements 38 and 40.

As the alignment elements 38 and 40 engage, the connector 24 of the component 12 engages the connector 28 of the component 14. More particularly and still referring to FIG. 2B, the hooks 27 of the component 12 first contact the conjunctiva 100. The hooks 27 may optionally pierce the conjunctiva 100. Upon contacting the first opening 30 of the recess 29 of the component 14, the hooks 27 of the barb 25 flex in a direction toward each other as the hooks 27 are pushed through the first opening 30. Once the beveled surfaces 26 of the hooks 27 clear the first opening 30 of the recess 29, the hooks 27 deflect back to their original position within the second opening 32 of the recess 29. The hooks 27 are then captivated within the recess 29 of the component 14. Although not shown, if the hooks 27 did not pierce the conjunctiva 100, the hooks 27 would have pushed the conjunctiva 100 into the recess 29 of the connector 14.

Figure 8D:
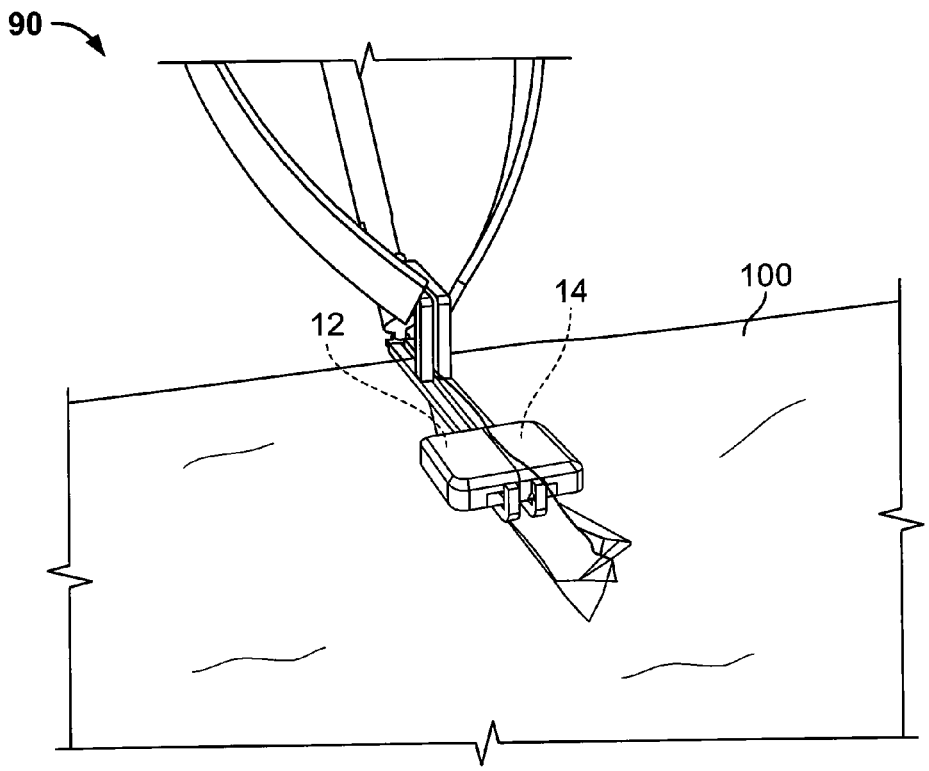
Figure 8E:
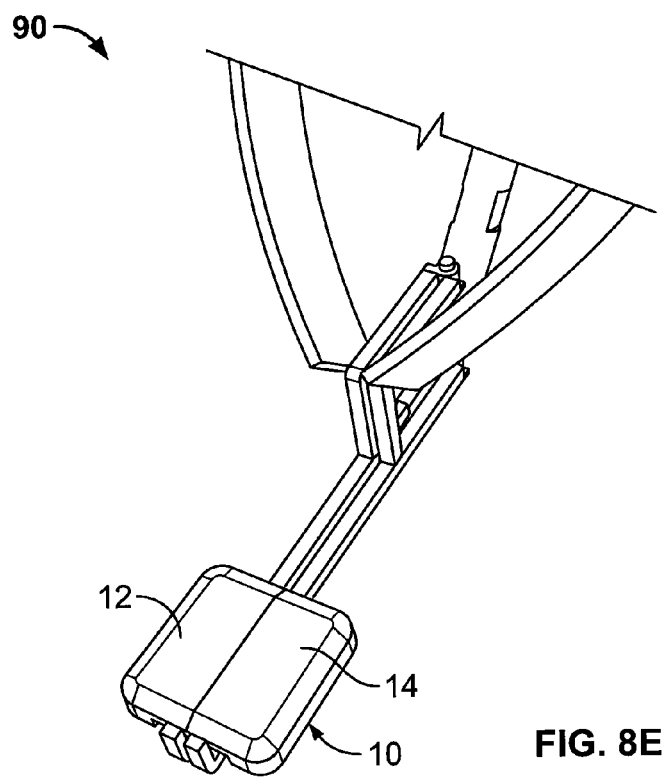

The component 12 is now secured to the component 14 forming the device 10 shown in FIGS. 8D-8F. Although not shown, the device 10 may include provisions for unlocking the components 12 and 14, such that the device 10 can be removed and/or repositioned, if necessary.

FIGS. 8D-8F depict perspective views of the components 12 and 14 of the device 10 in a mated configuration. In those figures, the free edges of the conjunctiva 100 are shown captured between the mating surfaces 20 and 22 of the components 12 and 14, respectively. Accordingly, the device 10 has substantially closed the opening 102 of the conjunctiva 100 and the conjunctiva 100 is maintained in a state of tension. Once the components 12 and 14 of the device 10 are mated together, the instrument 50 is removed from the implanted device 10.

FIGS. 8G through 8I depict an exemplary method of removing the instrument 50 from the implanted device 10. FIG. 8G depicts the elongate arms 70 and 72 of the instrument 50 pivoting away from each other. In practice, a medical practitioner slowly releases the force applied to the springs 60 of the instrument 50 thereby permitting the elongate arms 70 and 72 to pivot away from each other. Consequently, the tabs 86 of the elongate arms 70 and 72 translate away from the closed-ends 43 and 45 of the recesses 42 and 44, respectively.

Thereafter, the medical practitioner may gently lift the conjunctiva 100 and/or the implanted device 10 away from the eyeball and/or eyelid before proceeding to the next exemplary step shown in FIG. 8H. The connectors 24 and 28 of the device 10 are sufficiently robust to withstand the tension applied to the device 10 when the practitioner lifts the conjunctiva 100 away from the globe, scleral surface, or tarsus.

FIG. 8H depicts the elongated arms of the instrument translating in a downward direction with respect to the device 10. More particularly, once the medical practitioner lifts the conjunctiva 100 away from the eyeball and/or eyelid, the practitioner translates the elongate arms 70 and 72 of the instrument 50 in a downward direction, sliding the tabs 86 of the elongate arms 70 and 72 downward through the recesses 42 and 44 of the implanted device 10, respectively, until the tabs 86 are completely separated from the recesses 42 and 44.

FIG. 8I depicts the elongated arms of the instrument translating along the lower surface of the device of FIG. 1. While the conjunctiva 100 is still lifted away from the sclera and/or tarsus, the elongate arms 70 and 72 of the instrument 50 are retracted along the bottom surface of the implanted device 10 until the instrument 50 no longer resides beneath the conjunctive 100.

Figure 8J:
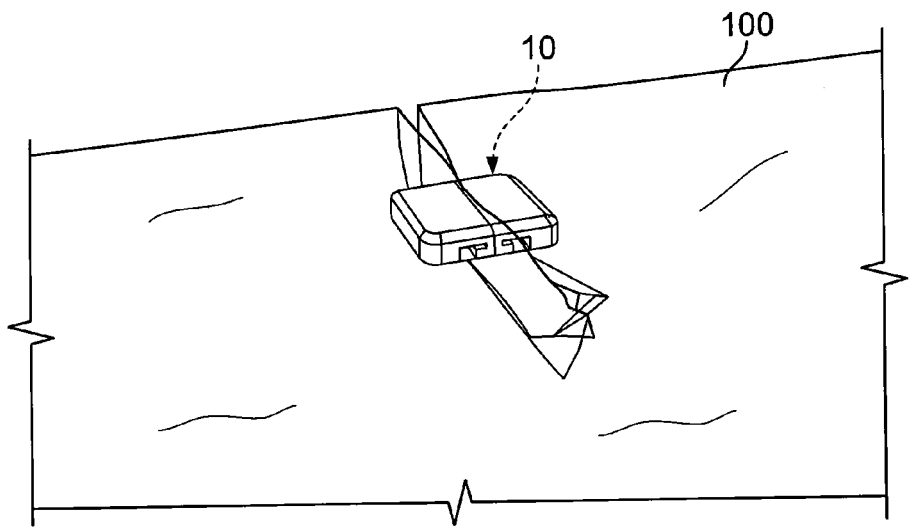

FIG. 8J depicts the opening 102 of the conjunctiva 100 substantially closed by the device 10. At this stage, the instrument 50 has been completely removed from the implanted device 10 and the conjunctiva 100. The implanted device 10 remains buried beneath the surface of the conjunctiva 100 until it completely dissolves and the free edges of the conjunctiva 100 heal together.

Figure 10:
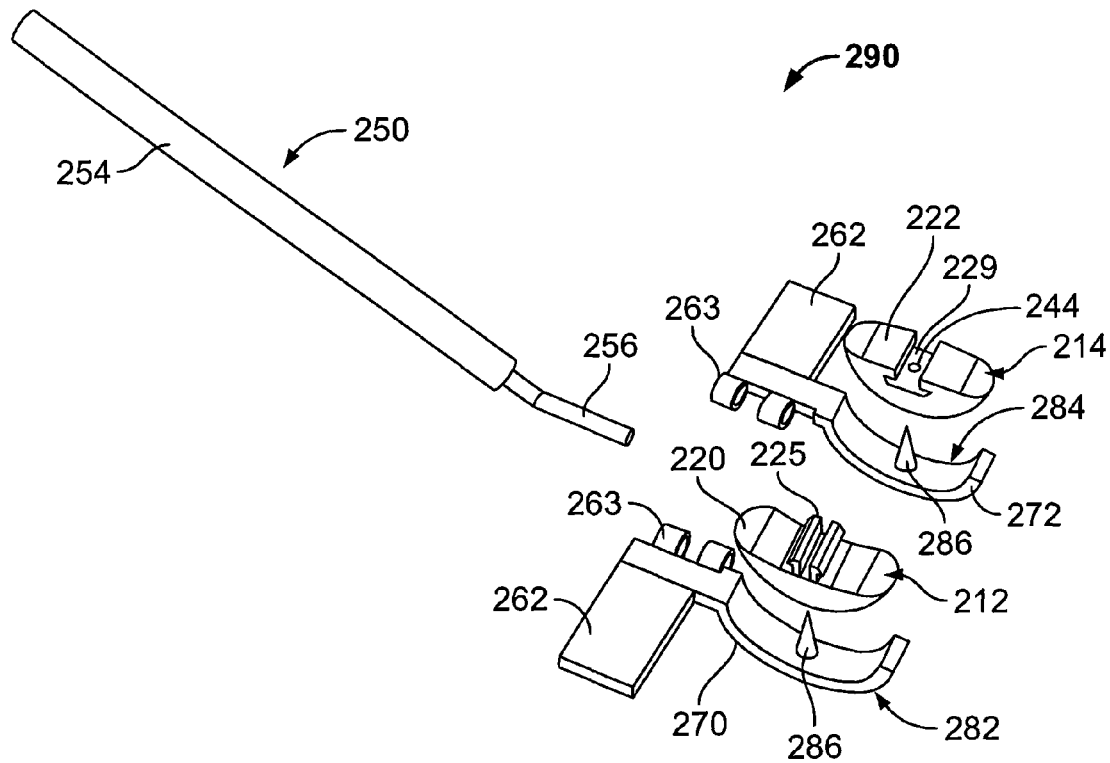
FIG. 10 depicts an exploded perspective view of yet another system for applying a surgical device to close a conjunctival opening, according to another exemplary embodiment of the invention.

FIG. 10 depicts an exploded perspective view of another system for applying a surgical device to close a conjunctival opening, according to yet another exemplary embodiment of the invention. The system depicted in FIG. 10 is designated by the numeral '290.' The system 290 generally includes an instrument 250 for implanting a surgical device 210 to close a conjunctival opening. The system 290 operates under the same general principles as the system 90 of FIG. 8A, with various exceptions.

The surgical device 210 includes a pair of mating components 212 and 214. In FIG. 10, the components 212 and 214 of the device 210 are shown separated. Each component 212 and 214 generally comprises a substantially semi-cylindrical shaped body. Alternatively, the overall shape of the components 212 and 214 may take any other form, such as rectangular, cylindrical, spherical, semi-spherical, cubic, conical, triangular, or any other desired shape. Like the components 12 and 14 depicted in FIG. 1, the components 212 and 214 are preferably low-profile, such that the device 210 does not irritate the eyeball, eyelid or the conjunctiva.

Each component 212 and 214 includes a mating surface 220 and 222, respectively. In assembled form of the device 210, the mating surfaces 220 and 222, respectively, are positioned to face one another and optionally contact each other. To facilitate mating of the components 212 and 214, each component includes a connector positioned on the mating surface that is configured for mating with a connector of a mating component, as described hereinafter.

The component 212 includes a connector in the form of a barb 225. Like the barb 25 of component 12 illustrated in FIG. 1, the barb 225 of the component 212 includes two hooks that extend from the mating surface 220 and are spaced apart along the mating surface 220 by a predetermined distance. The exterior corner of each hook includes a beveled surface for engaging a mating connector of the component 214, as described hereinafter.

The component 214 includes a connector that is configured to mate with the barb 225 of the component 12. The connector of the component 214 is provided in the form of a recess 229.

Like the barb and recess arrangement depicted in FIG. 2B, the barb 225 of the component 12 snaps into the recess 229 of the component 14. The connectors of the components 212 and 214 may also be generally referred to herein as a means for connection. The means for connection may be provided in the form of a clip, a pin, a catch, a clamp, a latch, a key, a detent, a fastener, a barb, a hole, an adhesive, a magnet, a slot, a recess, a track, a dovetail or any other device known in the art.

In practice, the components 212 and 214 of the device 210 are loaded onto the instrument 250. To accomplish this, each component 212 and 214 includes a hole 244 extending through the entire thickness thereof for releasably receiving a piercing element 286 of the instrument 250, as described hereinafter.

FIG. 10 depicts the instrument 250 (shown exploded) for implanting the surgical device 210 to close a conjunctival opening. The instrument is generally represented by the numeral '250.' The instrument 250 includes a long cylindrical handle 254 for grasping by a medical practitioner. Like the handle 54 of FIGS. 3-7, the handle 254 may have ergonomic and aesthetic properties such as a gripping surface formed on or applied thereto to enhance tactile feel. A stem 256 extends from the base of the handle 254.

Two elongate arms 270 and 272 are pivotably coupled to the stem 256 of the handle 254. Each elongate arm 270 and 272 includes a hinge 263 that is pivotably mounted to the stem 256 of the handle 254. A finger tab 262 extends from each elongate arm 270 and 272 enabling a medical practitioner to manually pivot the elongate arms 270 and 272 with respect to each other. Accordingly, the exterior surfaces of the finger tabs 262 may include a gripping surface formed on or applied thereto to enhance tactile feel.

Each elongate arm 270 and 272 includes a receiving portion 282 and 284, respectively, that is configured for releasably receiving and accommodating a component 212 and 214 of the device 210, respectively. The component 212 may be arranged in the receiving portion 282 and the component 214 may be arranged in the receiving portion 284, as shown in FIG. 10, or vice versa. Although not shown, each elongate arm 270 and 272 may include a plurality of receiving portions 282 and 284, respectively, for implanting multiple devices in a single surgical maneuver.

Each receiving portion 282 and 284 comprises a U-shaped bend formed along a distal portion of an elongate arm 270 and 272, respectively. The interior surfaces of the receiving portions 282 and 284 are substantially semi-circular for receiving the exterior surfaces of the components 212 and 214, respectively.

A piercing element 286 extends outwardly from the interior surface of each receiving portion 282 and 284. Each piercing element 286 is located in the center of the receiving portion 282 and 284. The piercing elements 286 are provided and sized for engaging a hole 244 of a component 212 or 214 of the device 210. Although not explicitly shown, the piercing elements 286 are axially offset with respect to one another such that the piercing elements 286 do not contact when the mating surfaces 220 and 222 of the components 212 or 214, respectively, are brought together. In practice, the piercing elements 286 of the instrument 250 pierce the conjunctiva upon mating the components 212 and 214 of the device 210.

Although not shown, the piecing element 286 of each receiving portion 282 and 284 may be positioned adjacent the components 212 and 214, as opposed to being positioned through the hole 244 of the components 212 and 214. Additionally, although not shown, the shape of each piercing element 286 may vary from that shown. For example, the sharp end of both piercing elements 286 may be bent, angled or curved toward each other to enhance the steps of capturing the conjunctiva and drawing the conjunctiva between the mating surfaces 220 and 222 of the components 212 or 214, respectively.

Use of the system 290 does not differ substantially from that described with reference to FIGS. 8A through 8J. In practice, the medical practitioner seats the components 212 and 214 onto respective receiving portions 282 and 284 of the instrument 250, such that the piercing elements 286 are positioned through the holes 244 of the device 210. Once the medical practitioner positions the loaded instrument beneath the conjunctiva, the medical practitioner pivots the finger tabs 262 toward each other thereby drawing the elongate arms 270 and 272 together.

Upon rotating the finger tabs 262, the piercing elements 286 of the instrument 250 pierce the conjunctiva thereby drawing the conjunctiva between the mating surfaces 220 and 222 of the components 212 and 214, respectively. The finger tabs 262 are rotated toward each other until the barb 225 of the component 212 is captured within the recess 229 of the component 214.

Once the device 210 is implanted, the medical practitioner pivots the finger tabs 262 of the instrument 250 away from each other until the piercing elements 286 completely disengage the components 212 and 214. Thereafter, the medical practitioner gently lifts the conjunctiva with forceps and retracts the instrument 250 from the implanted device 210. Unlike the removal procedure of instrument 50 shown in FIGS. 8G through 8I, the instrument 250 need not be retracted beneath the implanted device 210. Thus, removing the instrument 250 from the device 210 may be perceived by a medical practitioner to be a simpler procedure than removing the instrument 50 from the device 10.

Figure 11:
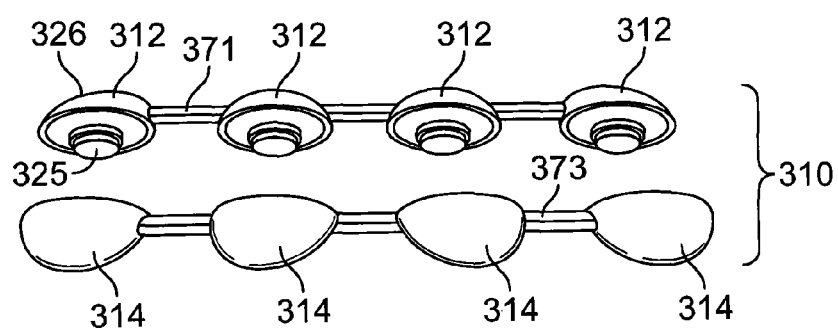
FIG. 11 depicts a surgical device for closing a conjunctival opening, according to another exemplary embodiment of the invention.

FIG. 11 depicts a surgical device for closing a conjunctival opening, according to another exemplary embodiment of the invention. The surgical device is generally designated by the numeral '310.' The surgical device includes daisy-chained pairs of mating components 312 and 314. Each daisy-chain includes four components 312 and 314. The number of components 312 and 314 may vary. In FIG. 11, the components 312 and 314 of the device 310 are shown separated. Each component 312 and 314 generally comprises a substantially semi-ovular shaped body. Alternatively, the overall shape of the component 312 and 314 may take any other form, such as rectangular, cylindrical, semi-cylindrical, spherical, semi-spherical, cubic, conical, triangular, or any other desired shape. Like the components 12 and 14 depicted in FIG. 1, the components 312 and 314 are preferably low-profile, such that the device 310 does not irritate the eyeball, eyelid or the conjunctiva.

Each component 312 and 314 includes a mating surface and a connector positioned on the mating surface that is configured for mating with a connector of a mating component. The component 312 includes a connector in the form of a barb 325. The exterior corner of each barb 325 includes a beveled surface for engaging a recess (not shown) of the component 314. Once the barb 325 is engaged in a mating recess of the component 314, the components 312 and 314 are secured together.

The four daisy-chained components 312 are linked in series by ribs 371. Similarly, the four daisy-chained components 314 are also linked in series by ribs 373. By linking the components together, multiple components 312 and 314 may be applied by one instrument (not shown) to conjunctival tissue in a single surgical maneuver. The daisy-chained components 312 and 314 are especially useful for rapidly closing a large conjunctival opening.

In practice, it may occur that only a few of the component pairs 312 and 314 are implanted. In such an event, after implanting the device 310, the components 312 and 314 that were not implanted are severed from the implanted device 310 by trimming the appropriate ribs 371 and 373 and removing the superfluous components 312 and 314.

Although this invention has been described with reference to exemplary embodiments and variations thereof, it will be appreciated that additional variations and modifications can be made within the spirit and scope of this invention. Numerous variations, changes and substitutions will occur to those skilled in the art without departing from the spirit of the invention. For example, the closure of conjunctiva is one example in which the devices described herein are useful, but the devices described herein and methods of use of those devices are applicable to any surgical procedure in which a superficial elastic layer of tissue requires closure. The invention has potential for use in applications outside of ophthalmology, particularly in surgical fields involving mucous membranes such as the oral mucosa. Accordingly, it is intended that the appended claims cover all such variations as fall within the spirit and scope of the invention.

What is claimed:

1. A device for closing an opening in conjunctival tissue comprising:
   a first component configured to be positioned beneath conjunctival tissue, the first component comprising:
      an absorbable body including a mating surface;
      a means for connection positioned on said mating surface;
      a means for alignment positioned on said mating surface and spaced from said connection means;
      recesses formed on opposing surfaces of the absorbable body that are configured to receive an instrument for applying said absorbable body to close the opening in conjunctival tissue, said mating surface being separate from and extending between said opposing surfaces,
   a second component configured for mating with the first component and configured to be positioned beneath conjunctival tissue, said second component comprising:
      an absorbable body including a mating surface;
      a means for connection positioned on said mating surface of said second component, said connection means of said second component being configured for connecting said connection means of said second component to said connection means of said first component and for mating said second component to said first component;
      a means for alignment positioned on said mating surface of said second component and spaced from said connection means of said second component, said alignment means of said second component being configured for aligning said alignment means of said second component with said alignment means of said first component and for aligning said second component with said first component; and
      recesses formed on opposing surfaces of the absorbable body of the second component that are configured to receive the instrument for applying said absorbable body of the second component to close the opening in conjunctival tissue, said mating surface of the second component being separate from and extending between said opposing surfaces of the second component,
   wherein upon alignment between said alignment means of said first component and said second component and connection between said connection means of said first component and said connection means of said second component, the first and second components are secured together and conjunctival tissue can be captivated between the mating surfaces of said first component and said second component,
   wherein each recess of the first and second components is L-shaped and includes an open end for receiving the instrument that extends perpendicularly to a closed end for securing the instrument in the recess.

2. The device of claim 1, wherein said connection means of said first component comprises a barb.

3. The device of claim 2, wherein said connection means of said second component comprises a recess that is configured to matingly receive said barb of said first component.

4. The device of claim 1, wherein said alignment means of said first component comprises semi-spherical detents.

5. The device of claim 4, wherein said alignment means of the second component comprises semi-spherical depressions that are configured to receive said semi-spherical detents of said first component.

6. The device of claim 1, wherein said connection means of said first component and said second component are selected from the group consisting of a clip, a pin, a catch, a clamp, a latch, a key, a detent, a fastener, a barb, a hole, an adhesive, a magnet, a slot, a recess, a track, and a dovetail.

7. The device of claim 1, wherein said alignment means of said first component and said second component are selected from the group consisting of a post, a hole, a slot, a recess, a pin, a catch, a clamp, a latch, a key, a detent, a fastener, a barb, a hole, a track, and a dovetail.

8. The device of claim 1, wherein a cross-section of the closed end of each recess is less than a cross-section of the open end of each recess.

9. A device for closing an opening in conjunctival tissue comprising:
   a pair of mateable components configured to be positioned beneath conjunctival tissue, each component having an absorbable body including a mating surface, a connector positioned on said mating surface that is configured for mating with the connector of a mating component, an alignment element positioned on said mating surface and spaced from said connector for aligning the alignment element of a mating component, and recesses formed on opposing surfaces of each mateable component that are configured to receive an instrument for applying said device to close an opening in conjunctival tissue, said mating surface being separate from and extending between said opposing surfaces;
   said connector of one component being either a recess or a barb configured for engaging said recess and said connector of the other component being the other of said barb or said recess,
   wherein upon alignment between the alignment elements of the components and connection between the connectors of the components, the components are mated together and conjunctival tissue can be captivated between the mating surfaces of said components,
   wherein each recess of the first and second components is L-shaped and includes an open end for receiving the instrument that extends perpendicularly to a closed end for securing the instrument in the recess.

10. The device of claim 9, wherein the absorbable bodies of each component are composed of polyglactin.

11. The device of claim 9, wherein a cross-section of the closed end of each recess is less than a cross-section of the open end of each recess.

* * * * *